US007129035B2

(12) United States Patent
Goldstein et al.

(10) Patent No.: US 7,129,035 B2
(45) Date of Patent: Oct. 31, 2006

(54) METHOD OF PRESERVING TISSUE

(75) Inventors: Steven Goldstein, Atlanta, GA (US); Joseph Hamby, Atlanta, GA (US); Steven P. Walsh, Marietta, GA (US); Kirby S. Black, Acworth, GA (US)

(73) Assignee: CryoLife, Inc., Kennesaw, GA (US)

( * ) Notice: Subject to any disclaimer, the term of this patent is extended or adjusted under 35 U.S.C. 154(b) by 0 days.

(21) Appl. No.: 10/734,096

(22) Filed: Dec. 11, 2003

(65) Prior Publication Data
US 2004/0209235 A1 Oct. 21, 2004

Related U.S. Application Data

(60) Provisional application No. 60/432,957, filed on Dec. 11, 2002.

(30) Foreign Application Priority Data
Dec. 11, 2003 (WO) ............... PCT/US03/39838

(51) Int. Cl.
*A01N 1/02* (2006.01)
*A01N 1/00* (2006.01)
*C12N 5/00* (2006.01)

(52) U.S. Cl. ............... 435/1.3; 435/1.1; 435/325; 435/374

(58) Field of Classification Search ............ 435/1.1, 435/1.3, 2
See application file for complete search history.

(56) References Cited

U.S. PATENT DOCUMENTS

| | | | |
|---|---|---|---|
| 2,832,689 A | 4/1958 | Proctor et al. | |
| 3,808,113 A | 4/1974 | Okamura et al. | 204/159.12 |
| 4,155,331 A * | 5/1979 | Lawrence et al. | 119/214 |
| 4,179,338 A | 12/1979 | Gordon | |
| 4,456,589 A | 6/1984 | Holman et al. | 424/95 |
| 4,620,908 A | 11/1986 | Van Duzer | 204/157.68 |
| 4,798,611 A | 1/1989 | Freeman, Jr. | 623/66 |
| 4,890,457 A | 1/1990 | McNally et al. | 435/2 |
| 5,012,503 A | 4/1991 | Nambu et al. | 378/64 |
| 5,071,741 A | 12/1991 | Brockbank | 435/1 |
| 5,096,553 A | 3/1992 | Ross et al. | 204/157.15 |
| 5,110,722 A | 5/1992 | Brockbank et al. | 435/1 |
| 5,122,110 A | 6/1992 | McNally et al. | 600/36 |
| 5,131,850 A | 7/1992 | Brockbank | 435/1 |
| 5,145,769 A | 9/1992 | McNally et al. | 435/1 |
| 5,257,692 A | 11/1993 | Heacox | 206/210 |
| 5,279,964 A * | 1/1994 | Chrisope | 435/307.1 |
| 5,283,034 A | 2/1994 | Okrongly et al. | 422/22 |
| 5,328,821 A * | 7/1994 | Fisher et al. | 435/1.3 |
| 5,362,442 A | 11/1994 | Kent | 422/22 |
| 5,403,834 A * | 4/1995 | Malfroy-Camine et al. | 514/185 |
| 5,485,496 A | 1/1996 | Lee et al. | 378/64 |
| 5,609,866 A | 3/1997 | Khan et al. | 424/78.25 |
| 5,677,019 A * | 10/1997 | Carstairs et al. | 428/22 |
| 5,730,933 A | 3/1998 | Peterson | 422/22 |
| 5,989,498 A | 11/1999 | Odland | 422/22 |
| 6,140,123 A * | 10/2000 | Demetriou et al. | 435/374 |
| 6,171,549 B1 | 1/2001 | Kent | 422/22 |
| 6,346,216 B1 | 2/2002 | Kent | 422/22 |
| 6,365,338 B1 | 4/2002 | Bull et al. | 435/1.1 |
| 6,908,591 B1 | 6/2005 | MacPhee et al. | |
| 2001/0000804 A1 | 5/2001 | Goldstein et al. | 623/23.72 |

FOREIGN PATENT DOCUMENTS

| | | |
|---|---|---|
| WO | WO 93/11666 A1 | 6/1993 |
| WO | WO 96/27287 A1 | 9/1996 |
| WO | WO 99/60849 A1 | 12/1999 |
| WO | WO 02/32225 A2 | 4/2002 |
| WO | WO 03/026704 A1 | 4/2003 |
| WO | WO 03/092745 A1 | 11/2003 |

OTHER PUBLICATIONS

Campbell, D.G. et al., *Sterilization of HIV by Gamma Irradiation. A Bone Allograft Model.*, Int. Orthop, vol. 18: No. 3, pp. 172-176, Jun. 1994.
Cooper, D.E. et al., "Contaminated Patellar Tendon Grafts: Incidence of Positive Cultures and Efficacy of an Antibiotic Solution Soak—an In Vitro Study", Arthroscopy vol. 7, No. 3, pp. 272-274, 1991.
Dichtelmuller, H. et al., "Validation of Virus Inactivation and Removal for the Manufacturing Procedure of Two Immunoglobulins and a 5% Serum Protein Solution Treated with Beta-Propiolactone", Biologicals, vol. 21: No. 3, pp. 259-268. Sep. 1993.
Erickson, G.A. et al., "Detection and Elimination of Adventitious Agents in Continuous Cell Lines", Dev Biol Stand, vol. 70, pp. 59-66, 1989.
Goertzen, M.J. et al., "Anterior Cruciate Ligaments Reconstruction Using Cryopreserved Irradiated Bone-ACL-Bone-Allograft Transplants", Knee Surg Sports Traumatol Arthors, vol. 4: No. 3, pp. 190, 1996.
Keller, K.M., "Action of Hydrogen Peroxide on Degradation of DNA After Irradiation in Escherichia coli", Int J Radiat Biol Relat Stud Phys Chem Med, vol. 31: No. 5, pp. 407-413, May 1977.
Lafferty, H.H. et al., "The Analysis of Decay Curves", Clin Sci Mol Med, vol. 52: No. 1, pp. 97-101, Jan. 1977.
Lee, S.F. et al., "Induction Of c-Jun Protooncogene Expression By Hydrogen Peroxide Through Hydroxyl Radical Generation and $p60^{SRC}$ Tyrosine Kinase Activation", Free Radic Biol. Med. vol. 21, No. 4, pp. 437-448, 1996.
Lindsey, M.E. et al., "Quantitation of Hydroxyl Radical During Fenton Oxidation Following a Single Addition of Iron and Peroxide", Chemosphere, vol. 41, No. 3, pp. 409-417, Aug. 2000.
Liu, B. et al., "Mouse Antibody Response Following Repetitive Injections of Gamma-Irradiated Human Placenta Collagen", Chin Med Sci J. (China), vol. 9: No. 2, pp. 100-103, Jun. 1994.

(Continued)

*Primary Examiner*—Sandra E. Saucier
*Assistant Examiner*—Lora E Barnhart
(74) *Attorney, Agent, or Firm*—Brinks Hofer Gilson & Lione (57) ABSTRACT

This invention relates to the sterilization and preservation of tissue for storage. More specifically, the invention relates to a method of using a solution to form a preserved tissue. The solution includes a radical scavenger at a concentration believed to reduce the damage to the tissue that could otherwise occur during sterilization with ionizing radiation.

28 Claims, 2 Drawing Sheets

OTHER PUBLICATIONS

Mello Filho, A.C. et al., "*Cell Killing and DNA Damage by Hydrogen Peroxide are Mediated by Intracellular Iron*", Biochem J, vol. 218: No. 1, pp. 273-275, Feb. 1984.

Mulford, D.J. et al., "*Glutathione-S-Transferase-Mediated Methylthio Displacement and Turnover in the Metabolism of Pentachlorothioanisole by Rats*", Xenobiotica, vol. 21, No. 5, pp. 597-603, May, 1991.

Patchen, M.L. et al., "*Glucan: Mechanisms Involved in its "Radioprotective" Effect*", J. Leukocyte Biol. vol. 42: No. 2, pp. 95-105, Aug. 1987.

Price, C.C. et al., "*The Thermal Decomposition of Dimsyl Ion in Dimethyl Sulfoxide*", J. Org Chem, vol. 34: No. 9, pp. 2503-2506, Sep. 1969.

Repine, J.E. et al., "*Hydrogen Peroxide Kills Staphylococcus aureus by Reacting with Staphylococcal Iron to Form Hydroxyl Radical*", J Biol Chem, vol. 256: No. 14, pp. 7094-7096, Jul. 1981.

Reszka, K.J. et al., *Free Radical Reactions Photosensitized by the Human Lens Component, Hynurenine: an EPR and Spin Trapping Investigation*, Free Radic. Biol. Med. vol. 20, No. 1, pp. 23-24, 1996.

Rimbach, G. et al., "*Liver and Colon Oxidant Status in Growing Rats Fed Increasing Levels of Dietary Iron*", J. Trace Elem. Med. Biol. vol. 11, No. 2, pp. 99-104, Jun. 1997.

Schiller, J. et al., "*Reactivity of Cartilage and Selected Carbohydrates with Hydroxyl Radicals: an NMR Study to Detect Degradation Products*", Free Radic Res, vol. 28: No. 2, pp. 215-228, Feb. 1998.

Shen, B. et al., "*Increased Resistance to Oxidative Stress in Transgenic Plants by Targeting Mannitol Biosynthesis to Chloroplasts*", Plant Physiol., vol. 113, No. 4, pp. 1177-1183, Apr. 1997.

Vasin, M.V., "*Radioprotective Efficiency of Indraline With Local Gamma Radiation of the Skin*", Radiats Biol Radioecol (Russian), vol. 38: No. 1, pp. 42-54, Jan.-Feb. 1998.

"*Virus Inactivation in Plasma Products*", Current Studies in Hematology and Blood Transfusion, vol. 56, pp. 1-158, no year.

Weiss, H. et al., "*Oxygen Depletion in Cells Irradiated at Ultra-High Dose-Rates and at Conventional Dose-Rates*", Int J. Radiat Biol., Relat Stud Phys Chem Med, vol. 26: No. 1, pp. 17-29, Jul. 1974.

Willkommen, H. et al., "*Theoretical Considerations on Viral Inactivation or Elimination*", Dev Biol Stand, vol. 81, pp. 109-116, 1993.

Zhang, L. et al., "*Effect of a Combined Gamma Irradiation and Parylene Plasma Treatment on the Hydrolytic Degradation of Synthetic Biodegradable Sutures*", J. Biomed Mater Res, vol. 27: No. 11, pp. 1425-1441, Nov. 1993.

Abot, K. et al., "*Dimethylsulfoxide Increases the Survival and Lysosomal Stability of Mouse Peritoneal Macrophages Exposed to Low-LET Ionizing Radiation and/or Lioniclron in Culture*", Virchows Arch B Cell Pathol Incl Mol Pathology, vol. 46: No. 4, pp. 307-320, 1984.

Angell, W.W. et al., "*Long-Term Follow-Up of Viable Frozen Aortic Homografts A Viable Homograft Valve Bank*", J. Thorac Cardiovasc. Surg. vol. 93: No. 6, pp. 815-822, Jun. 1987.

Antoku, S., "*Chemical Protection of Bacteria and Cultured Mammalian Cells by Sulfur-Containing Compounds*", J. Radiat Res (Tokyo), vol. 16: No. 1, pp. 28-36, Mar. 1975.

Antoku, S. et al., "*Effect of Oxygen on Bacteria and Cultured Mammalian Cells Irradiated in the Frozen State*", Int'l. J. Radiat. Biol. Relat. Stud. Phys. Chem. Med., vol. 32: No. 2, pp. 145-152, Aug. 1977.

Aparicio, S.R. et al., "*Light and Electron Microscopy Studies on Homograft and Heterograft Heart Valves*", J Path, vol. 115, pp. 147-162, 1975.

Arroyo, C.M. et al., "*ESR Study of Electron Transfer Reactions Between Gamma-Irradiated Pyrimidines, Adriamycin and Oxygen*", Free Radic Bio Med, vol. 9: No. 3, pp. 191-197, 1990.

Babbs, C.F. et al., "*Colorimetric Assay for Methanesulfinic Acid in Biological Samples*", Analytical Biochemistry vol. 163, pp. 67-73, 1987.

Babbs, C.F. et al., *Detection and Quantitation of Hydroxyl Radical Using Dimethyl Sulfoxide as Molecular Probe*, Methods in Enzymology, vol. 186, pp. 137-147, 1990.

Babbs, C.F. et al., *Scatchard Analysis of Methane Sulfinic Acid Production From Dimethyl Sulfixide; A Method To Quantify Hydroxyl Radical Formation In Physiologic Systems*, Free Radical Biology & Medicine, vol. 6, pp. 493-503, 1989.

Babbs, C.F., "*Free Radicals and the Etiology of Colon Cancer*", Free Radic. Biol Med, vol. 8, No. 2, pp. 191-200, 1990.

Bailey, A.J., "*Effect of Ionizing Radiation on Connective Tissue Components*", Int Rev. Connect Tissue Res., vol. 4, pp. 233-281, 1968.

Bakke, J.E. et al., "*Isotope Dilution Assay for Urinary Methanesulfinic and Methanesulfonic Acids: Application to Detection of Methylthio Turnover*", Biomed. Environ. Mass Spectrom, vol. 18, No. 12, pp. 1096-1098, Dec. 1989.

Bartova, E. et al., "*The Influence of the Cell Cycle, Differentiation and Irridiation on the Nuclear Location of the abl, bcr and cy-myc Genes in Human Leukemic Cells*", Leuk Res, vol. 24: No. 3, pp. 233-241, Mar. 2000.

Beach, P.M. et al., "*Aortic Valve Replacement with Frozen Irradiated Homograft. Long-Term Evaluation*", Circulation, vol. 45: No. 5, Suppl 1: pp. 29-35, May 1972.

Beach, P.M. et al., "*Frozen Irradiated Aortic Valve Homografts: Long-Term Evaluation*", NY State J. Med, vol. 73: No. 5, pp. 651-654, Mar. 1973.

Beamer, R.L., "*Biochemical Interactions of Dimethyl Sulfoxide II Lactate Dehydrogenase-Catalyzed Reactions*", J Pharm Sci, vol. 62: No. 8, pp. 1384-1386, Aug. 1973.

Bechtold, J.E. et al., "*The Effects of Freeze-Drying and Ethylene Oxide Sterilization on the Mechanical Properties of Human Pateller Tendon*", American Journal of Sports Medicine, vol. 22: No. 4, pp. 562-566, 1994.

Bedford, J.S. et al., "*Dose-Rate Effects in Synchronous Mammalian Cells in Culture*", Radiat Res, vol. 54: No. 2, pp. 316-327, May 1973.

Belkoff, S.M. et al., "*Microstructurally Based Model Analysis of Gamma-Irradiated Tendon Allografts*", J Orthop Res, vol. 10: No. 3, pp. 461-464, May 1992.

Belov, A.A. et al., "*The Effect of Gamma Irradiation on the Enzyme Activity of Collalitin Druing Storage*", Radiobiologiia (USSR), vol. 30: No. 4, pp. 519-521, Jul.-Aug. 1990.

Bender, E. et al., "*The Inactivation of Mycoplasmas and Bacteria in Calf Serum by 60Co Gamma Rays*" Arch Exp Veterinarmed, vol. 43: No. 5, pp. 783-788, 1989.

Bender, E. et al., "*The Use of 60CO-Gamma Ray-Sterilized Calf Serum in Cell Culture*", Arch Exp Veterinarmed, vol. 44: No. 3, pp. 481-488, 1990.

Bennett, C.B. et al., "*DNA Damage and Biological Expression of Adenovirus: A Comparison of Liquid Versus Frozen Conditions of Exposure to Gamma Rays*", Radiat Res, vol. 120: No. 1, pp. 102-112, Oct. 1989.

Bingci L. et al., "*Mouse Antibody Response Following Repetitive Injections of Gamma-Irradiated Human Placenta Collagen*" Chin Med Sci J, vol. 9, No. 2, pp. 100-103, 1994.

Blanchy, B.G., "*Immobilization of Factor XIII on Collagen Membranes*", J. Biomed Mater Res, vol. 20: No. 4, pp. 469-479, Apr. 1986.

Blank, G. et al., "*Comparison of Resistenace of Fungal Spores to Gamma and Electron Beam Radiation*", Int J Food Microbiol, vol. 26: No. 3, pp. 269-277, Aug. 1995.

Blankevoort, L. et al., "*Knee Joint Modeling: Parameters and Validity*", Second World Congress of Biomechanics, Jul. 10-15, 1994, Amsterdam, The Netherlands.

Bodnar, E. et al., "*Long-Term Performance of Homograft and Autograft Valves*", Artif Organs, vol. 4: No. 1, pp. 20-23, Feb. 1980.

Bodnar, E. et al., "*Viable and Non-Viable Aortic Homografts in the Subcoronary Position: A Comparative Study*", Ann Thorac Surg, vol. 47: No. 6, pp. 799-805; discussion pp. 804-805, Jun. 1989.

Bogers, A.J.J.C. et al., "*Long-Term Results of the Gamma-Irradiation-Preserved Homograft Monocusp for Transannular Reconstruction of the Right-Ventricular Outflow Trace in Tetralogy of Fallot*", Thorac. Cardiovasc. Surgeon, vol. 42, pp. 337-339, 1994.

Bohidar, H.B. et al., "*Kinetics of Sol-Gel Transition in Thermoreversible Gelation of Gelatin*", J. Chem. Phys. vol. 98, No. 11, pp. 8970-8977, Jun. 1993.

Bolin, S.R., "*Methods for Detection and Frequency of Contamination of Fetal Calf Serum with Bovine Viral Diarrhea Virus and Antibodies Against Bovine Viral Diarrhea Virus*", J Vet Diagn Invest, vol. 3: No. 3, pp. 199-203, Jul. 1991.

Bray, R.C. et al., "*Reactions of Dimethylsulfoxide Reductase in the Presence of Dimethyl Sulfide and the Structures of the Dimethyl Sulfide-Modified Enzyme*", Biochemistry, vol. 40, No. 33, pp. 9810-9820, Aug. 21, 2001.

Bruck R. et al., "*The Hydroxyl Radical Scavengers Dimethylsulfoxide and Dimethylthiourea protect Rats Against Thioacetamide-induced fulminant hepatic failure*", J. Hepatol, vol. 31, No. 1 pp. 27-38, Jul. 1999.

Bruck, R. et al., "*Prevention of Hepatic Cirrhosis in Rats by Hydroxyl Radical Scavengers*", J. Hepatol, vol. 35, No. 4, pp. 457-464, Oct. 2001.

Butler, D.L. et al., "*Effects of Gamma Irradiation on the Biomechanics of Patellar Tendon Allografts of the ACL in the Goat*", 37th Annual Meeting, Orthopaedic Research Society, Mar. 4-7, 1991, Anaheim, CA.

Campalani, G. et al., "*Aortic Valve Replacement with Frozen Irradiated homografts. An 18-Year Experience*", Eur J. Cardiothorac Surg., vol. 3: No. 6, pp. 558-561, 1989.

Cederbaum, A.I. et al., "*Oxidation of Isopropanol by Rat Liver Microsomes: Possible Role of Hydroxyl Radicals*" Biochem Pharmacol, vol. 30: No. 8, pp. 825-831, Apr. 1981.

Cheung, D.T. et al., "*The Effect of Gamma-Irradiation on Collagen Molecules, Isolated Alpha-Chains, and Crosslinked Native Fibers*", Journal of Biomedical Materials Research, vol. 24: No. 5, pp. 581-589, May 1990.

Chiu, S.M., et al., "*Modification of DNA Damage in Transcriptionally Active vs Bulk Chromatin*", Int. J. Radiat Oncol. Biol. Phys. vol. 12, No. 8, pp. 1529-1532, Aug. 1986.

Chu, C.C. et al., "*The Effect of Gamma Irradiation on the Enzymatic Degradation of Polyglycolic Acid Absorbable Sutures*", J. Biomed Mater Res, vol. 17: No. 6, pp. 1029-1040, Nov. 1983.

Chu, C.C. et al., "*Kluver-Bucy Syndrome: Report of a Case with Nasopharyngeal Cancer after Irradiation and Chemotherapy*", Chin Med J. (Taipei) 1994: 54: pp. 432-435.

Chu, C.C. et al., "*Scanning Electron Microscopic Study of the Hydrolytic Degradation of Poly(glycolic acid) Suture*", J. Biomed Mater Res, vol. 16: No. 4, pp. 417-430, Jul. 1982.

Cooper, A.J. et al., "*Enzymatic Reactions of Methionine Sulfoximine. Conversion to the Corresponding Alpha—imino and Alpha-keto Acids and to Alpha-ketobutyrate and Methane Sulfinimide*", J. Biol. Chem., vol. 251, No. 21, pp. 6674-6682, Nov. 10, 1976.

Daragan, V.A. et al., "*Specific Binding of Ethanol to Cholesterol in Organic Solvents*" Biophys J, vol. 79: No. 1, pp. 406-415, Jul. 2000.

Davydov, R. et al., "*An EPR Study to the Dinuclear Iron Site in the Soluble Methane Monooxygenase from Methylococcus Capsulatus (Bath) Reduced by One Electron at 77K: The Effects of Component Interactions and the Binding of Small Molecules to the Diiron(III) Center*", Biochemistry, vol. 38: No. 13, pp. 4188-4197, Mar. 1999.

De Deyne, P. et al., "*Some Effects of Gamma Irradiation on Patellar Tendon Allografts*", Connect Tissue Res, vol. 27: No. 1, pp. 51-62, 1991.

deLara, C.M. et al., "*The Effect of Dimethyl Sulfoxide on the Induction of DNA Double-Strand Breaks in V79-4 Mammalian Cells by Alpha Particles*", Radiat Res. vol. 144: No. 1, pp. 43-49, Oct. 1995.

Dela Rosa, et al., "*The Effect of Gamma-Radiation on Smoked Fish Using Short-Term Mutagenicity Assays*", Mutat Res., vol. 223, No. 3, pp. 303-307, Jul. 1989.

Dimitrijevic, B., "*The Tissue Bank in Wickfield*", Stomatol Glas Srb, vol. 21: No. 1, pp. 67, Jan.-Feb. 1974.

Dinara, S. et al., *Effects of Supplementation with Free-Radical scavengers on the survival and Fertilization Rates of Mouse Cryopreserved Oocytes*, Elsevier Science B.V., Amsterdam, 2001 BIOTECHNO Online!

Donnelly, R.J. et al., "*Gamma-Radiation of Heart Valves at 4 C; a Comparative Study Using Techniques of Histochemistry and Electron and Light Microscopy*", Thorax, vol. 28: No. 95, pp. 95-101, 1973.

Duliu, O.G. et al., "*EPR Investigation of the Gamma-Ray Irradiated Natural and Tanned Collagen*", Appl Radiat Isot, vol. 54: No. 6, pp. 887-891, Jun. 2001.

Eder, E. et al., "*The Influence of the Solvents DMSO and Ethanol on the Genotoxicity of Alpha, Beta-Unsaturated Aldehydes in the SOS Chromotest*", Mutat Res., vol. 516, No. 1-2, pp. 81-89, Apr. 26, 2002.

Erickson, G.A. et al., "*Viral Contamination of Fetal Bovine Serum Used for Tissue Culture: Risks and Concerns*", Dev Biol Stand, vol. 75, pp. 173-175, 1991.

Farzaneh, F. et al., "*DNA Repair in Human Promyelocytic Cell Line, HL-60*", Nucleic Acids Res, vol. 15, No. 8, pp. 3503-3513, Apr. 1987.

Fast Blue BB Salt, Materials Safety Data Sheet http://www.property.orst.edu/property/msds/DATA/5381.htm, May 24, 2002, 2 pages.

Feder, S.M. et al., "*Biomechanical and Biochemical Changes in Human Tendon Allografts Due to 4Mrad of Gamma Irradiation*", 40th Annual Meeting, Orthopaedic Research Society, Feb. 21-24, 1994, New Orleans, LA, 1 page.

Feder, S.M. et al., "*Irradiated ACL Allografts: Changes in Mechanical Properties Over Time*", 38th Annual Meeting, Orthopaedic Research Society, Feb. 17-20, 1992, Washington, D.C.., 1 page.

Fideler, B.M., "*Gamma Irradiation: Effects on Biomechanical Properties of Human Bone-Patellar Tendone-Bone Allografts*", The American Journal of Sports Medicine, vol. 23: No. 5, pp. 643-646, 1995.

Fideler, B.M. et al., "*Effects of Gamma Irradiation on the Human Immunodeficiency Virus. A Study in Frozen Human Bone-Patellar Ligament-Bone Grafts Obtained from Infected Cadavera*", J Bone Joint Surg Am, vol. 76: No. 7, pp. 1032-1035, Jul. 1994.

Fukui S. et al., "*High-Performance Liquid Chromatographic Determination of Methanesulphinic Acid as a Method for the Determination of Hydroxyl Radicals*", J. Chromatogrphy, vol. 630, Nos. 1-2, pp. 187-193, Feb. 5, 1993.

Geesin, J.C., et al., "*Regulation of Collagen Synthesis by Ascorbic Acid: Characterization of the Role of Ascorbate-Stimulated Lipid Peroxidation*", Arch Biochem Biophys, vol. 290: No. 1, pp. 127-132, Oct. 1991.

Gerbode, Frank et al., "*Proceedings of The First International Workshop on Tissue Valves*", Annals of Surgery vol. 172, Supplement, pp. 1-24, Jul. 1970.

Gibbons, M.J. et al., *Dose-Dependent Effects of Gamma Irradiation on the Material Properties of Frozen Bone-Patellar Tendon-Bone Allografts*, 35th Annual Meeting, Orthopaedic Research Society, Feb. 6-9, 1989, Las Vegas NV.

Gibbons, M.J. et al., "*Effects of Gamma Irradiation on the Initial Mechanical and Material Properties of Goat Bone-Patellar Tendon-Bone Allografts*", J Orthop Res, vol. 9: No. 2, pp. 209-218, Mar. 1991.

Giordano, Joseph M. et al., "*A Comparison of Autografts and Frozen, Irradiated Homografts in Canine Femoral Venous Reconstruction*", Surgery, vol. 81: No. 1, pp. 100-104, Jan. 1977.

Godette, G.A. et al., "*Biomechanical Effects of Gamma Irradiation on Fresh Frozen Allografts in Vitro*", Gamma Irradiation, vol. 19: No. 8, Aug. 1996.

Goertzen, M.J., "*Anterior Cruciate Ligament Reconstruction Using Cryopreserved Irradiated Bone-ACL-Bone-Allograft Transplants*", Knee Surg Sports Traumatol Arthros, vol. 2: No. 3, pp. 150-157, 1994.

Goertzen, M.J. et al., "*Sterilisation of Canine Anterior Cruciate Allografts by Gamma Irradiation in Argon Mechanical and Neurohistological Properties Retained One Year After Transplantation*", J. Bone Joint Surg Br (England), vol. 77: No. 2, pp. 205-212, Mar. 1995.

Gogus, A. et al., "*Allogeneic Cruciate Ligament Replacement. Perspectives and Initial Clinical Results*", Unfallchirurg (Germany), vol. 96: No. 2, pp. 93-99, Feb. 1993.

Gonzalez-Lavin, L. et al., "Homograft Aortic Valve Replacement", J of Thoracic and Cardiovascular Surgery, vol. 60: No. 1, pp. 1-12, Jul. 1970.

Goulas, A.E. et al., "Effect of High-Dose Electron Beam Irradiation on the Migration of DOA and ATBC Plasticizers from Food-Grade PVC and PVDC/PVC Films, Respectively, Into Olive Oil", J Food Prot, vol. 61: No. 6, pp. 720-724, Jun. 1998.

Grecz, N. et al. "Radiation Sterilization of Surgical Instruments with a Consideration of Metal Shielding on Sterilization Efficiency", Am J Infect Control, vol. 15: No. 3, pp. 101-106, Jun. 1987.

Gunning, A.J. et al., "Preservation and Function of Heterologous Aortic Valves", Thorax, vol. 26, p. 179, 1971.

Harris, Paul D. et al., "Factors Modifying Aortic Homograft Structure and Function", Surgery vol. 63: No. 1, pp. 45-52, Jan. 1968.

Haut, R.C. et al., "Order of Irradiation and Lyphilization on the Strength of Patellar Tendon Allografts", 35th Annual Meeting, Orthopaedic Research Society, Feb. 6-9, 1989, Las Vegas, NV.

Hiemstra, H. et al., "Inactivation of Human Immunodeficiency Virus by Gamma Irradiation and its Effect on Plasma and Coagulation Factors", Transfusion, vol. 31: No. 1, pp. 32-39, Jan. 1991.

House, C. et al., "Inactivation of Viral Agents in Bovine Serum by Gamma Irradiation", Can J Microbiol, vol. 36: No. 10, pp. 737-740, Oct. 1990.

Ijiri, S. et al., "Effect of Sterilization on Bone Morphogenetic Protein", J. Orthop Res, vol. 12: No. 5, pp. 628-636, Sep. 1994.

Ingegneri, A. et al., "An 11-Year Assessment of 93 Flash-Frozen Homograft Valves in the Aortic Position", Thorac Cardiovasc Surg. vol. 27: No. 5, pp. 304-307, Oct. 1979.

Jackson, D.W., et al., "Anterior Cruciate Ligament Reconstruction Using Patella Tendon Autograft and Allograft—An Experimental Study in Goats", 37th Annual Meeting, Orthopaedic Research Society, Mar. 4-7, 1991, Anaheim, California, p. 208.

Jackson, D.W. et al., "Intraarticular Reaction Associated with the Use of Freeze-Dried, Ethylene Oxide-Sterilized Bone-Patella Tendon-Bone Allografts in the Reconstruction of the Anterior Cruciate Ligament", Am. J. Sports Med., vol. 18: No. 1, pp. 1-10, Jan.-Feb. 1990.

Jacob, Stanley, W., Current Status of Dimethyl Sulfoxide (DSMO), Mar. 2002. http://www.dmso.org/articles/information/pjacob.htm, 2p., Jun. 17, 2002.

Jacob, Stanley, W. "Pharmacology of DMSO", http://www.dmso.org/articles/information/pherschler.htm, pp. 1-13, Jun. 17, 2002.

Jahnke, L.S., "Measurement of Hydroxyl Radical-Generated Methane Sulfinic Acid by High-Performance Liquid Chromatography and Electrochemical Detection", Anal Biochem, vol. 269, No. 2, pp. 273-277, May 1999.

Jones, G.D., et al., "A Comparison of DNA Damages Produced Under Conditions of Direct and Indirect Action of Radiation", Int. J. Radiat Biol. vol. 66, No. 5, pp. 441-445, Nov. 1994.

Jones, G.D., et al., "Yield of Strand Breaks as a Function of Savenger Concentration and LET for SV40 Irradiated with 4He Ions", Int. J. Radiat Biol. vol. 136, No. 2, pp. 190-196, Nov. 1993.

Kadiiska, M.B. et al., "Iron Supplementation Generates Hydroxyl Radical in Vivo. An ESR Spin-Trapping Investigation", J. Clin. Invest., vol. 96, No. 3, pp. 1653-1657, Sep. 1995.

Katz, R.W. et al., "Radiation-Sterilized Insoluble Collagenous Bone Matrix is a Functional Carrier of Osteogenin for Bone Induction", Calcif Tissue Int, vol. 47: No. 3, pp. 183-185, Sep. 1990.

Kennedy, A.R., "Water Structure versus Radical Scavenger Theories as Explanations for the Suppressive Effects of DMSO and Related Compounds on Radiation-Induced Transformation in Vitro", Carcinogenesis, vol. 8: No. 5, pp. 683-688, May 1987.

Kerboull, P. et al., "In Vitro Study of the Role of Various Preservation Methods on Mechanical Properties of Allografts of the Patellar Tendon", Chirurgie, vol. 117: No. 9, pp. 751-762, 1991.

Klein, S.M. et al., "The Interaction of Hydroxyl Radicals with Dimethylsulfoxide Produces Formaldehyde", FEBS Lett, vol. 116, No. 2, pp. 220-222, Jul. 28, 1980.

Klein, S.M. et al., "Production of Formaldehyde During Metabolism of Dimethyl Sulfoxide by Hydroxyl Radical Generating Systems", Biochemistry, vol. 20, No. 21, pp. 6006-6012, Oct. 13, 1981.

Koch, C.J. et al., "The Oxygen-Enhancement Ratio for Reproductive Death Induced by 3H or 125I Damage in Mammalian Cells", Int. J. Radiat Biol Relat Stud Phys Chem Med, vol. 28: No. 5, pp. 417-425, Nov. 1975.

Kurahashi, M. et al., "Effect of Diethyldithiocarbamate on Diabetogenic Action of Alloxan in Rats", Diabetes Res Clin. Prac., vol. 19, No. 1, pp. 39-47, Jan. 1993.

Kyvsgaard, N.C., et al., "Effect of Two Virus Inactivation Methods; Electron Beam Irradiation and Binary Ethylenimine Treatment on Determination of Reproductive Hormones in Equine Plasma", Acta Vet Scan, vol. 38: No. 3, pp. 225-233, 1997.

Lawson, L.D. et al., "Identification and HPLC Quantitation of the Sulfides and Dialk(en)yl Thiosulfinates in Commercial Garlic Products", Plant Med, vol. 57: No. 4, pp. 363-370, Aug. 1991.

Leslie, H.W., et al., "Donation, Banking, and Transplantation of Allograft Tissues", Nurs Clin North Am, vol. 24: No. 4, pp. 891-905, Dec. 1989.

Limaye, L.S., et al., Bone Marrow Cryopreservation: Improved Recovery Due to Bioantioxidant Additives in the Freezing Solution, Elsevier Science B.V., Amsterdam, BIOTECHNO Online! 1997.

Maeda, A. et al., "Changes of Mechanical Properties After Solvent Preservation And/or Gamma Irradiation for Tendon Allografts", 37th Annual Meeting, Orthopaedic Research Society, Mar. 4-7, 1991, Anaheim, CA.

Maeda, A. et al., "Effects of Solvent Preservation with or without Gamma Irradiation on the Material Properties of Canine Tendon Allografts", Orthop Res, vol. 11: No. 2, pp. 181-189, Mar. 1993.

Malm, James R. et al., "An Evaluation of Aortic Valve Homografts Sterilized by Electron Beam Energy", J. of Thoracic and Cardiovascular Surgery, vol. 54: No. 4, pp. 471-477, Oct. 1967.

Manninen, M. et al., "Evaluation of a Microbiological Method for Detection of Irradiation of Spices", Z Lebensm Unters Forsch, vol. 192: No. 3, pp. 226-229, Mar. 1991.

Mecs I. et al., "Effect of Storage and 60Co Irradiation on the Antiviral Activity and Subtype Pattern of Native Human Interferon-Alpha Preparations", Acta Virol, vol. 33: No. 2, pp. 177-182, Mar. 1989.

Medical Device Sterilization; Gamma Processing Technology; obtained at www.sterigenics.com/medical/medical.htm.

Meeker, Irving A. et al., "Low-Temperature Sterilization of Organic Tissue by High-Voltage Cathode-Ray Irradiation", Science, vol. 114, pp. 283-285, Sep. 1951.

Meeker, Irving A. et al., "Sterilization of Frozen Aterial Grafts by High-Voltage Cathrode-Ray Irradiation", Surgery, vol. 50: No. 1, Jul. 1951.

Merwitz, O., et al., "Oxygen Effect and Influence of Buffer on Radiation-Induced Tritium Cleavage from phage-T2-DNA-(methyl-3H)in Aqueous Solution", Radiat. Environ Biophys., vol. 24, No. 4, pp. 239-249, 1985.

Mikhailov, M.I. et al., "Effect of Gamma Radiation on the Components of Hepatitis B Virus and the Delta Antigen", Vopr Virusol, vol. 32: No. 1, pp. 68-71, Jan.-Feb. 1987.

Miller, M.D. et al., "The Use of Allograft Techniques and Results", Clin Sports Med, vol. 12: No. 4, pp. 757-770, Oct. 1993.

Milligan, J.R. et al., "Characterization of the Reaction Rate Coefficient of DNA with the Hydroxyl Radical", Radiat Res, vol. 146: No. 5, pp. 510-513, Nov. 1996.

Milligan, J.R. et al., "Methylperoxyl Radicals as Intermediate in the Damage to DNA Irradiated in Aqueous Dimethyl Sulfoxide with Gamma Rays", Radiat Res, vol. 146: No. 4, pp. 436-443, Oct. 1996.

Milligan, J.R. et al., "The Difference that Linear Energy Transfer Makes to Precursors of DNA Strand Breaks", Radiat. Res., vol. 145: No. 4, pp. 442-448, Apr. 1996.

Milligan, J.R. et al., "Yield of Single-Strand Breakds Due to Attack on DNA by Scavenger-Derived Radicals", Radiat Res, vol. 137, No. 3, pp. 295-299, Mar. 1994.

Miyazaki, T., et al., "Radioprotective Effects of Dimethyl Sulfoxide in Golden Hamster Embryo Cells Exposed to Gamma Rays at 77 K.K. Radical Formation as Studied by Electron Spin Resonance", Radiat Res Vol. 124, No. 1, pp. 66-72, Oct. 1990.

Monboisse, J.C. et al., "Collagen Degradation by Superoxide Anions in Pulse and Gamma Radiolysis Biochim", Biophys Acta, pp. 29-35, Apr. 1988.

Monboisse, J.C. et al., "*Effect of Oxy Radicals on Several Types of Collagen*", Int J. Tissue React, vol. 6: No. 5, pp. 385-390, 1984.

Moore, C.H., et al., "*Analysis of Homograft Valve Failure in 311 Patients Followed up to 10 Years*", Ann Thorac Surg. vol. 20: No. 3, pp. 274-281, Sep. 1975.

Mutluer, B. et al., "*Effects of Gamma Irradiation on Aflatoxins*", Lebensm Unters Forsch, vol. 185, No. 5, pp. 398-401, Nov. 1987.

Nair, P.D., "*Currently Practised Sterilization Methods—Some Inadvertent Consequences*", J Biomater Appl, vol. 10: No. 2, pp. 212-235, Oct. 1995.

O'Brien, Mark F. et al., "*The Viable Cryopreserved Allograft Aortic Valve*", J. Cardiac Surg, 2[Suppl], pp. 153-167, 1987.

Oleinick, N.L. et al., "*Nuclear Structure and the Microdistribution of Radiation Damage in DNA*", Int. J. Radiat. Biol., vol. 66: No. 5, pp. 523-529, Nov. 1994.

Olson, E.J. et al., "*Clinicals Use of Fresh, Frozen Soft Tissue Allografts*", Orthopedics, vol. 15: No. 10, pp. 1225-1232, Oct. 1992.

Pacifico, A.D. et al., "*Homografts for Replacement of the Aortic Valve*", Supplement I to Circulation, vols. ILV and XLVI, May 1972.

Parker, R. et al., *Elasticity of Frozen Aortic Valve Homografts*, Cardiovasc Res., vol. 11: No. 2, pp. 156-159, Mar. 1977.

Perrella, F.W., et al., "*Effects of 12-O-tetradecanoylphorbol-13-acetate and Mezerein on Gamma Radiation-Induced DNA Repair in Resting Bovine Lymphocytes*", Cancer Lett, vol. 15, No. 1, pp. 87-93, Jan. 1982.

Preuss, T. et al., "*Comparison of Two Different Methods for Inactivation of Viruses in Serum*", Clin Diagn Lab Immunol, vol. 4: No. 5, pp. 504-508, Sep. 1997.

Raoul, S. et al., "*Gamma Irradiation of 2'-Deoxyadenosine in Ocygen-Free Aqueous Solutions: Identification and Conformational Featurs of Formamidopyrimidine Nucleoside Derivatives*", Chem Res Toxicol, vol. 8: No. 7, pp. 924-933, Oct. 1995.

Rasmussen, T.J. et al., "*The Effects of 4 Mrad of Gamma Irradiation on the Initial Mechanical Properties of Bone-Patellar Tendon-Bone Grafts*", Arthroscopy, vol. 10: No. 2, pp. 188-197, Apr. 1994.

Rauch, G. et al., "*Biomechanical Study of the Tensile Strength of Lyophilized and Deep Frozen Human Achilles Tendons Following Gamma and Ethylene Oxide*", Orthop Ihre Grenzgeb (Germany), vol. 129: No. 5, pp. 393-399., Sep.-Oct. 1991.

Repine, J.E. et al., "*Dimethyl Sulfoxide Prevents DNA Nicking Mediated by Ionizing Radiation or Iron/Hydrogen Peroxide-Generated Hydroxyl Radical*", Proc Natl Acad Sci USA, vol. 78: No. 2, pp. 1001-1003, Feb. 1981.

Rodi, C.P. et al., "*Structure of Transcriptionally Active Chromatin: Radiological Evidence For Requirement of Torsionally Constrained DNA*", J. Cell Physiol., vol. 141, No. 2, pp. 346-352, Nov. 1989.

Roe, S.C. et al., "*Fate of Chemically Modified Bone-Ligament-Bone Allografts for Anterior Cruciate Ligament (ACL)Reconstruction*", 37th Annual Meeting, Orthopaedic Research Society, Mar. 4-7, 1991, Anaheim, California, p. 206.

Roe, S.C. et al., "*The Effect of Gamma Irradiation on a Xenograft Tendon Bioprosthesis*", Clin Mater, vol. 9: No. 3-4, pp. 149-154, 1992.

Rossi, C.R. et al., "*Viral Contamination of Bovine Fetal Lung Cultures and Bovine Fetal Serum*", Am J Vet Res, vol. 41: No. 10, pp. 1680-1681, Oct. 1980.

Rousseau C.F. et al., *In vitro cytocompatibility of porcine type I atelocollagen crosslinked by oxidized glycogen*, Biomaterials, vol. 23: No. 6, pp. 1503-1510, Mar. 2002.

Salai, M. et al., "*Electron Microscopic Study on the Effects of Different Preservation Methods for Meniscal Cartilage*", Ann Transplant, vol. 2: No. 1, pp. 52-54, 1997.

Scaduto, R.C. Jr., et al., "*Oxidation of DMSO and Methanesulfinic Acid by the Hydroxyl Radical*", Free Biol Med, vol. 18: No. 2, pp. 271-277, Feb. 1995.

Shaw, J.M. et al., "*Vitrification Properties of Solutions of Ethylene Glycol in Saline Containing PVP, Ficoll, or Dextran*", Cryobiology vol. 35, Article No. CY972043, pp. 219-229, (1997).

Shelton, W.R. et al., "*Use of Allografts in Knee Reconstruction: I Basic Science Aspects and Current Status*", J. Am Acad. Orthop. Surg., vol. 6: No. 3, pp. 165-168, May-Jun. 1998.

Silvaggio, V.J. et al., "*The Induction of IL-1 Freeze Dried Ethylene Oxide Treated Bone-Patellar Tendon-Bone Allograft Wear Particles. An in Vitro Study*", 37th Annual Meeting, Orthopaedic Research Society, Mar. 4-7, 1991, Anaheim, CA.

Singh, D.R. et al., "*Effect of Dimethyl Sulfoxide (DMSO)on Radiation-Induced Heteroallelic Reversion in Dipoloid Yeast*" Muta Res, vol. 37: Nos. 2-3, pp. 193-200, Nov. 1976.

Sjoberg, A.M. et al., "*Methods for Detection of Irradiation of Spices*", Z Lebensm Unters Forsch, vol. 190: No. 2, pp. 99-103, Feb. 1990.

Smith, C.W. et al., "*Effects of Irradiation and Hydration Upon the Mechanical Properties of Tendon*", Journal of Materials Science, Materials in Medicine, vol. 7: No. 11, pp. 645-650, Nov. 1996.

Smith, C.W. et al., "*Mechanical Properties of Tendons: Changes with Sterilization and Preservation*", J. Biomech Eng Trans ASME, vol. 118: No. 1, pp. 56-61, 1996.

Smith, J.B. et al., "*Quantitative Effects of Iron Chelators on Hydroxyl Radical Production by the Superoxide-Driven Fenton Reaction*", Free Radic Res Commun, vol. 8: No. 2, pp. 101-106, 1990.

Smoukov, S.K. et al., "*Product Binding to the Diiron(III)and Mixed-Valence Diiron Centers of Methane Monooxygenase Hydroxylase Studied by (1,2)H and (10)F ENDOR Spectroscopy*", J. Am. Chem. Soc., vol. 124: No. 11, pp. 2657-2663, Mar. 2002.

Steckler, D. et al., "*Tissue Banking: The Rose of the Regional Blood Centre: An American Experience in Minnesota*", Med Lab Sci, vol. 48: No. 2, pp. 147-154, Apr. 1991.

Steiner, M.G. et al., "*Hydroxyl Radical Generation by Postichemic Rat Kidney Slices in Vitro*", Free Radic Biol. Med. vol. 9, No. 1, pp. 67-77, 1990.

Steiner, M.G. et al., "*Quantitation of the Hydroxyl Radical by Reaction with Dimethyl Sulfoxide*", Arch Biochem Biophys, vol. 278: No. 2, pp. 478-481, May 1990.

Sterling, J.C. et al., "*Allograft Failure in Cruciate Ligament Reconstruction. Follow-up Evaluation of Eighteen Patients*", Am. J. Sports Med., vol. 23: No. 2, pp. 173-178, Mar.-Apr. 1995.

Stoyanovsky, D.A. et al., "*ESR and HPLC-EC Analysis of the Interaction of Hydroxyl Radical with DMSO: Rapid Reduction and Quantification of POBN and PBN Nitroxides*", Anal. Chem., vol. 71, No. 3, pp. 715-721, Feb. 1, 1999.

Suh, H. et al., "*Evaluation of the Degree of Cross-Linking in UV Irradiated Porcine Valves*", Yonsei Med J., vol. 40: No. 2, pp. 159-165, Apr. 1999.

Tan, A.J.K. et al., "*The Effects of Sterilization and Storage Treatments on the Stress-Strain Behavior of Aortic Valve Leaflets*", The Annals of Thoracic Surgery, vol. 22: No. 2, pp. 188-194, Aug. 1976.

Tarandy, D.I. et al., "*An unusual Intrinsic Complication of a Patellar Tendon Allograft and Recommendations for Tissue Banking*", Arthroscopy, vol. 11: No. 4, pp. 475-477, Aug. 1995.

Tesoriere, L. et al., "*Melatonin Protects Human Red Blood Cells from Oxidative Hemolysis: New Insights into the Radical-Scavenging Activity*", J. Pineal Res., vol. 27, No. 2, pp. 95-105, Sep. 1999.

Thomas, F.C. et al., "*Gamma Ray Inactivation of Some Animal Viruses Can*", J Comp Med, vol. 45: No. 4, pp. 397-399, Oct. 1981.

Thomas, F.C. et al., "*Inactivation by Gamma Irradiation of Animal Viruses in Simulated Laboratory Effluent*", Appl Environ Microbiol, vol. 43: No. 5, pp. 1051-1056, May 1982.

Turner, W.D. et al., "*An In Vitro Study of the Structural Properties of Deep-Frozen Versus Freeze-Dried, Ethylene Oxide-Sterilized Canine Anterior Cruciate Ligament Bone-Ligament-Bone Preparations*", Clin Orthop (230), pp. 251-256, May 1988.

Ueda, T. et al., "*Effect of Dimethyl Sulfoxide Pretreatment on Activities of Lipid Peroxide Formation, Superoxide Dismutase and Glutathione Peroxidase in the Mouse Liver After Whole-Body Irradiation*",J Taxicol Sci, vol. 18: No. 4, pp. 239-244, Nov. 1993.

Vangsness, C.T., et al., "*Soft Tissue for Allograft Reconstruction of the Human Knee; A Survey of the American Association of Tissue Banks*", Am J Sports Med, vol. 24: No. 2, pp. 230-234, Mar.-Apr. 1996.

Vasin, M.V. et al., "*Radiation Protective Efficacy of Alpha-Adrenomimetics During Local Gamma Irradiation of the Skin*", Radiats Biol. Radioecol. (Russia), vol. 39: No. 2-3, pp. 249-253, Mar.-Jun. 1999.

Wall, Jarrod, *Antioxidants in Prevention of Reperfusion Damage of Vascular Endothelium*, TSMJ, vol. I, pp. 67-71, May 2000.

Ward, J.F. et al., *"Mammalian Cells are not Killed by DNA Single-Strand Breaks Caused by Hydroxyl Radicals from Hydrogen Peroxide"*, Radiat Res, vol. 103: No. 3, pp. 383-392, Sep. 1985.

Watts, M.E. et al., *"Fast Kinetics of the Oxygen Effect in Irradiated Mammalian Cells"*, Int J Radiat Biol Relat Stud Phys Chem Med, vol. 32: No. 2, pp. 195-199, Feb. 1978.

Westaby, S., et al., *"Aortic Root Replacement Modifications of Technique with Improvements in Technology"*, Eur J. Cardiothorac Surg, 6 Suppl 1:S44-8; discussion S49 1992.

White, J.M. et al., *"Sterilization of Teeth by Gamma Irradiation"*, J. Dent Res., vol. 73: No. 9, pp. 1560-1567, Sep. 1994.

Yahia, L.H. et al., *"The Irradiation Effect on the Initial Mechanical Properties of Meniscal Grafts"*, Biomed Mater Eng, vol. 3: No. 4, pp. 211-221, 1993.

Yates, J.R. et al., *"Studies in Depilation Use of Gamma-Radiation in the Sterilization of Sheepskins for Enzyme Depilation Studies"*, Radiat Res., vol. 34, No. 3, pp. 648-660, Jun. 1968.

Yoshimura, T. et al., *"Electron Spin Resonance Studies of Free Radicals in Gamma-Irradiated Golden Hamster Embryo Cells: Radical Formation at 77 and 295 K, and Radioprotective Effects of Vitamin C at 295 K"*, Radiat Res, vol. 136, No. 3, pp. 361-365, Dec. 1993.

Butler, D.L., et al., *"Gamma Irradiation Effects on Allograt Mechanics"*, Symposium Biomechanics of Joints and Ligaments, Thursday Jul. 14, 1994 Second World Congress of Biomechanics, vol. II, p. 89.

Buxton, George V. et al., *"Critical Review of Rate Constants for Reactions of Hydrated Electrons, Hydrogen Atoms and Hydroxyl Radicals (Oh/O)in Aqueous Solution"*, American Chemical Society and the American Institute of Physics for the National Bureau of Standards, p. 513-886 (1988).

Fuchs, James C.A. et al., *"Homograft Aortic Valves Supported by Nonthrombogenic Prosthetic Frames"*, Proceedings of the 23rd Annual Sessions of the Forum on Fundamental Surgical Problems, 53rd Clinical Congress of the American College of Surgeons, Chicago, IL, Oct. 1967, p. 118-119.

King, Michael H. et al., *"Importance of Technique in Sterilizing and Preserving Human Ortic Valves"*, Proceedings of the 23rd Annual Sessions of the Forum on Fundamental Surgical Problems, 53rd Clinical Congress of the American College of Surgeons, Chicago, IL, Oct. 1967, p. 119-121.

Marks, P.H. et al., *"Reconstruction of the Cruciate Ligaments with Allografts, Techniques, Results and Perspectives"*, Orthopade (1993) 22:386-391.

Schwartz, H.E. et al., *"Initial and Long Term Effects of Gamma Irradiation on Goat ACL Allograft Viscoelasticity"*, ASME, 1995, BED-vol. 29, 1995 Bioengineering Conference, pp. 205-206.

Wardman, Peter, *"Reduction Potentials of One-Electron Couples Involving Free Radicals in Aqueous Solution"*, American Chemical Society and the American Institute of Physics for the National Institute of Standards and Technology, p. 1637-1755 (1989).

Wright, K.A. et al., *"Co-operative Studies in the Use of Ionizing Radiation for Sterilization and Preservation of Biological Tissues: Twenty Years' Experience"*, IAEA-PL-333/12, (1970):107-18.

*"Virus Inactivation in Plasma Products"*, Current Studies in Hematology and Blood Transfusion, (1989) 56:1-158.

\* cited by examiner

METHOD OF PRESERVING TISSUE

REFERENCE TO RELATED APPLICATIONS

This application claims the benefit of U.S. Provisional Application No. 60/432,957, filed Dec. 11, 2002, which is incorporated by reference in its entirety.

BACKGROUND

This invention relates to the sterilization and cryopreservation of tissues for storage. The tissues may be harvested from human or animal subjects and are then processed and cryopreserved (frozen) for later implantation. Allograft tissues, including, but not limited to, heart valves and portions of heart valves, aortic roots, aortic walls, connective tissues including fascia and dura, vascular grafts (including arterial, venous, and biological tubes), and orthopedic soft tissues, such as boned- or non-boned tendons or ligaments, are often subjected to cryogenic preservation. In this manner, a ready supply of these valuable tissues can be made available for later implantation into mammals, especially humans. In addition, viable xenograft tissues from transgenic animals or tissues developed from human or non-human cells that may include differentiated cell types, stem cells, or genetically-modified cells of various origins may be appropriately processed, cryopreserved, and stored for later implantation.

In addition to living allograft, xenograft, or bio-engineered tissues, which may be cryopreserved, living tissues may be decellularized to render them acellular. While living tissues are often decellularized before cryopreservation, they can also be decellularized after cryopreservation and storage.

Generally, decellularization involves substantially reducing the living, non-structural constituents within the tissue. This may be achieved by first exposing the tissue to a hypotonic solution to lyse the cells and then subjecting the tissue to a nuclease treatment to degrade nucleic acids. A more detailed discussion of tissue decellularization may be found in U.S. Pub. No. US 2001/0000804 A1, which is incorporated by reference in its entirety, except that in the event of any inconsistent disclosure or definition from the present application, the disclosure or definition herein shall prevail.

Cryopreservation may be a preferred method of preserving living or decellularized tissue for extended storage. By cryopreserving a tissue in a suitable cryoprotectant, it may be possible to reduce the damage to the tissue that can occur during uncontrolled rate freezing, freeze-drying, and glutaraldehyde preservation methods. In contrast to uncontrolled rate freezing and freeze-drying, cryopreservation preferably involves the addition of one or more cryoprotectant containing solution to the tissue followed by a slower, controlled-rate freezing regimen, which can be adjusted to the particular requirements of each tissue to which it is applied. Cryoprotectants can limit cell or tissue damage due to the formation of ice (water) crystals during freezing and thawing.

In general, there are two requirements for the successful cryopreservation of living tissue. First, the harvested tissue should be frozen to a sufficiently low temperature so metabolic activity effectively ceases within the cell, without destroying the cell. Second, the cryopreservation and thawing regimens should have minimal effects on tissue cell viability and limit structural damage to the tissue. When decellularized tissue is cryopreserved, the primary focus is preventing damage to the structure of the extracellular matrix.

Varying cryoprotectant containing solutions have been used to cryogenically preserve biological tissues for later implantation. Some cryopreservation solutions use a combination of dimethylsulfoxide (DMSO) and Fetal Bovine Serum (FBS) with other constituents for tissue preservation. In these solutions, DMSO may provide interference with the ability of water to form ice crystals during freezing and radical scavenging. However, a disadvantage of DMSO based cryopreservation solutions is the unpleasant odor given off from irradiated solutions upon thawing. DMSO containing cryopreservation solutions can also demonstrate toxicity to living tissues above 4° C. This toxicity and the detailed thawing procedures required to limit its adverse affects on heart valves are described in U.S. Pat. No. 4,890,457, for example.

Because Fetal Bovine Serum is animal-derived, its use in cryopreservation solutions may introduce undesirable contaminants. In addition to the risk of contamination by bacteria and viruses, prion contamination is also possible. It is currently believed that Creutzfeldt-Jakob disease or variant bovine spongiform encephalopathy is transmitted through prions. Not only does FBS open the possibility of disease transmission, but due to the limited availability of cows believed free of prion transmitted disease, FBS can only be harvested from a limited number of herds in specific countries.

Unlike tissues sourced from other human individuals (allografts), which are classified by regulatory authorities as tissues intended for transplantation and whose processing includes procedures to reduce the risk of contamination by pathogenic agents, tissues sourced from different species (xenografts) are classified as medical devices and must be terminally sterilized prior to implantation. Sterilization techniques and conditions are preferably selected to provide a high level of assurance against contamination of the tissue with microbes, while limiting damage to the structure and function of the tissue. These same techniques may also reduce the activity or infectivity of other pathogenic agents, such as viruses, thus increasing the safety factor of the implantable device.

Decellularized tissues can be terminally sterilized using a variety of physical or chemical sterilants, or combinations thereof, including gamma radiation, electron-beam radiation, ethylene oxide, peracetic acid, β-propiolactone, povidone-iodine, or UV irradiation in the presence or absence of photosensitizers. Irradiation methods are preferred. One reason for this is that radiation can be administered to the tissue after final packaging, thus eliminating the necessity to accomplish and validate aseptic transfer of the tissue to its final packaging after sterilization.

Ionizing radiation, including gamma and electron-beam radiation, can be effective in killing a variety of microbial and pathogenic organisms, including bacteria, fungi, yeast, mold, mycoplasmas, parasites, and virus, when an appropriate cumulative dose of radiation is applied to the tissue. A more detailed discussion of gamma radiation and its use in the sterilization of preserved tissues may be found in U.S. Pat. No. 5,485,496, incorporated herein by reference in its entirety, except that in the event of any inconsistent disclosure or definition from the present application, the disclosure or definition herein shall prevail. A more detailed description of electron-beam radiation and its use in the sterilization of preserved tissues may be found in U.S. Pat. No. 5,989,498, also incorporated herein by reference in its entirety, except that in the event of any inconsistent disclosure or definition from the present application, the disclosure or definition herein shall prevail.

While ionizing radiation is convenient, different tissues have various degrees of susceptibility to damage by the energetic free-radicals that are generated during irradiation. While many types of damage may occur during irradiation, one of the most common is free-radical initiated cleavage of the primary amino acid sequence of the structural proteins. The effect of this scission is to cause tissue denaturation. Tissue denaturation can occur when the proteins of the tissue undergo conformational changes that disrupt the structure of the tissue. These structural changes can result in a loss of tissue function after implantation.

Tissue treatment with ionizing radiation may also alter tissue characteristics by producing crosslinking between tissue proteins. Crosslinking can occur when additional covalent bonds form between previously unbonded portions of one or more molecules. Energetic free-radicals are common initiators for radical crosslinking reactions.

Free-radicals or radicals are defined as highly energetic atoms or groups that possess an unpaired electron. The ability of radicals to damage tissues is well known. In addition to initiating crosslinking reactions, radicals can act as oxidizing or reducing agents that can further damage the tissue. Radical species may be generated by the irradiation of the tissue itself, the cryopreservation solution, or the packaging. While irradiation can form many radical species, oxygen and hydroxyl radicals are believed the most common species formed in aqueous solutions, such as cryopreservation solutions.

SUMMARY

In one aspect, the present invention provides a cryopreservation solution suitable for the cryopreservation of tissue. The solution includes a bio-compatible buffer, a cell-impermeant constituent, a cell-permeant constituent, and a radical scavenger.

In another aspect, the invention provides a sterile, implantable tissue that is suitable for extended storage.

In another aspect, the invention provides a method of cryopreserving a tissue for storage, including optional sterilization.

DETAILED DESCRIPTION

Definitions

Figure 1:
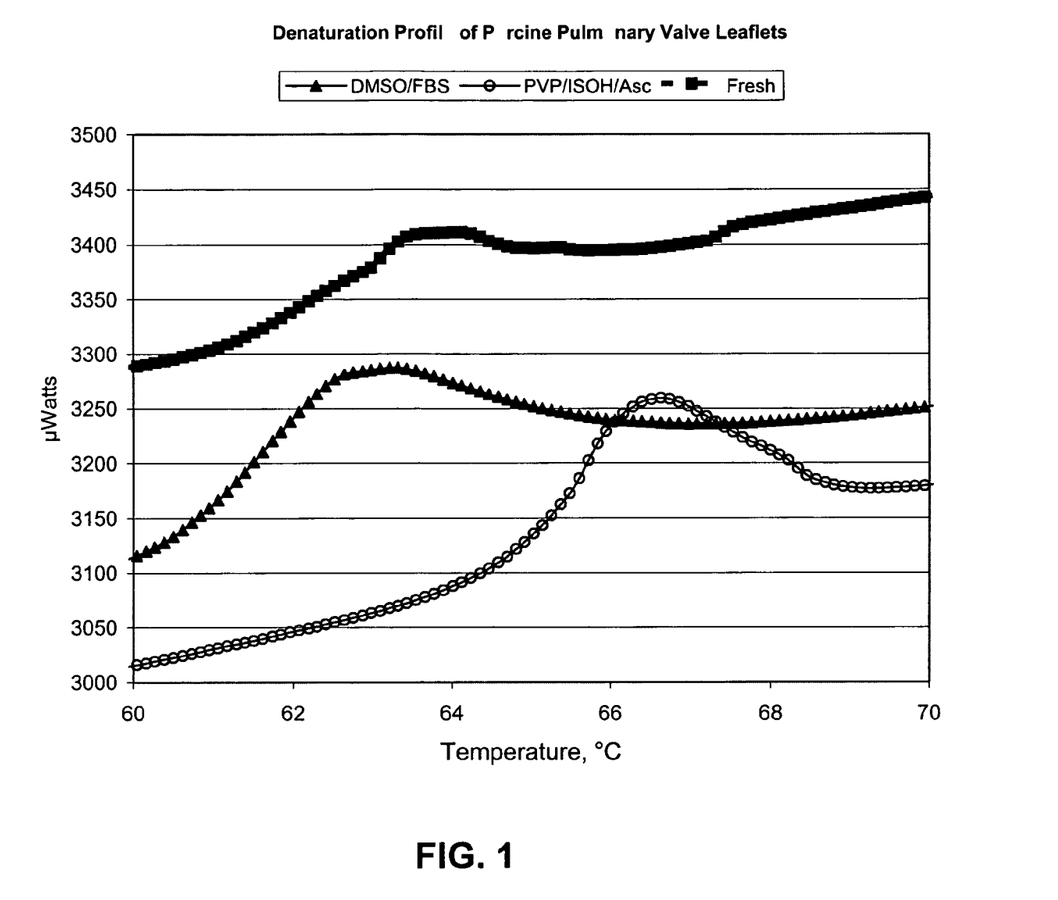
FIG. 1 shows the DSC denaturation profiles of (1) fresh porcine pulmonary valve leaflets, (2) thawed porcine pulmonary valve leaflets that were previously cryopreserved and irradiated in a DMSO/FBS cryopreservation solution, and (3) thawed porcine pulmonary valve leaflets that were previously cryopreserved and irradiated in a PVP/ISOH/Asc cryopreservation solution embodying aspects of the present invention.
Figure 2:
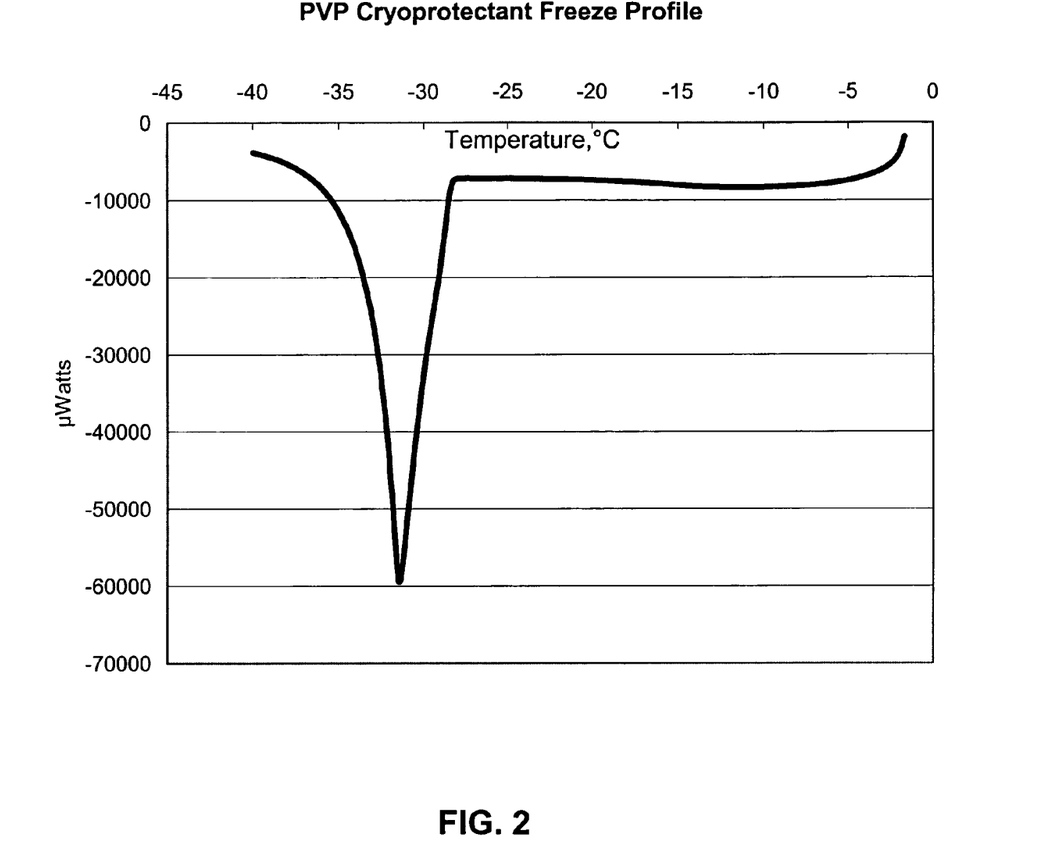
FIG. 2 shows the freezing profile of the PVP/ISOH/Asc solution embodying aspects of the present invention.

As used in the following specification and appended claims, the term "tissue" refers to any biological material that is harvested from one animal and implanted into the same species of animal (allograft) or another species of animal (xenograft). The tissue may be from a whole or partial organ, such as a heart valve or an aorta, or from a specific location in the animal, such as cartilage or a tendon from the knee joint.

As used in the following specification and appended claims, unless otherwise indicated, all percentages (%) are on a weight/volume basis.

As used in the following specification and appended claims, the term "solution" is intended to include solutions, dispersions, and suspensions. While true solutions lack an identifiable interface between their solubilized molecules and the solvent, the current cryopreservation solutions can have the characteristics of a solution, a dispersion, a suspension, or any combination of the three.

As used in the following specification and appended claims, the term "freezing" refers to lowering the temperature of the cryopreservation solution/tissue combination to below the freezing point of the cryopreservation solution.

As used in the following specification and appended claims, the term "extended storage" is at least three days, preferably, three days to ten years, and more preferably, one week to one year.

As used in the following specification and appended claims, the term "cryogenic temperature" is about −30° C. or less and more preferably about −70° C. or less. Cryogenic temperature also includes temperatures achieved by the use of liquid nitrogen, about −196° C., and temperatures achieved with solid carbon dioxide (dry ice) impregnated with liquid nitrogen.

EMBODIMENTS

In a preferred aspect, the invention provides a cryopreserved, sterile, and implantable tissue product that is suitable for extended storage. Preferably, the cryopreserved tissue product may be utilized as a replacement for defective tissues in mammals, particularly humans. Methods of replacing heart valves, tendons, ligaments, and vessels, for example, are well known to those of ordinary skill in the art.

In accordance with the present invention, novel cryopreservation solutions are used to cryopreserve an implantable tissue, which may then be sterilized with ionizing radiation. The solutions are suitable for preserving tissues for storage at cryogenic temperatures, including extended storage.

In one aspect, cryopreservation solutions embodying aspects of the present invention combine a cell-permeant constituent with a radical scavenger to replace DMSO. Surprisingly, the combination of a cell-permeant constituent with a radical scavenger in a cryopreservation solution embodying features of the present invention can protect tissues from freezing and irradiation damage without the need for DMSO. In one aspect, a preferred cryopreservation solution does not include DMSO.

The replacement of DMSO in cryopreservation solutions eliminates the formation of undesirable DMSO side-products. Thus, by replacing DMSO, cryopreservation solutions embodying aspects of the present invention can provide at least two significant advantages. First, the production of new, malodorous species during irradiation and thawing is significantly reduced. This unpleasant odor is believed attributable to the reaction of hydroxyl radicals with DMSO to produce methanesulfinic acid, methanesulfinate, and/or methanesulfonate. Thus, while DMSO is believed to react with the hydroxyl radicals, thereby reducing tissue damage during irradiation, undesirable odors are formed. A proposed mechanism for the reaction of hydroxyl radicals with DMSO may be found in Scaduto, R. C., Jr. *Oxidation of DMSO and*

*methanesulfinic acid by the hydroxyl radical.* Free Radic. Biol. Med. 1995; 18(2): 271–77. Second, the toxicity of DMSO at about 4° C. and above is eliminated, thus allowing for a simplified tissue freezing and thawing regimen, particularly in the case of viable tissues.

Preferably, cryopreservation solutions embodying aspects of the present invention rely on an extracellular-cryoprotectant to replace commonly used FBS. Thus, a cryopreservation solution may be prepared in accord with the present invention that does not include animal-derived constituents. In this context, a fully chemically defined and non-biological cryopreservation solution is a significant advantage due to the elimination of possible contamination from animal hosts and supply difficulties.

In accordance with the present invention, a novel method of cryopreserving and sterilizing a tissue is also described. In a preferred aspect, the tissue is placed in the cryopreservation solution and the temperature is slowly lowered until the tissue and the solution freeze. The solution may be added to the tissue in one or more steps, and solutions having varying concentrations of constituents may be added. Preferably, the tissue and cryopreservation solution are placed in a package prior to freezing. After freezing, the tissue may be irradiated for terminal sterilization and transferred to extended storage. Terminal sterilization can prevent the need for a later, potentially aseptic transfer. The tissue may be thawed prior to implantation in a mammal, generally a human.

In another aspect, the tissue is placed in the cryopreservation solution, irradiated, and stored at reduced temperature, but not cryopreserved. In this aspect, reduced temperature storage is preferably at refrigeration temperatures from about 0° C. to about 15° C. In another aspect, the tissue is placed in the cryopreservation solution, irradiated, and directly implanted without extended storage.

Biological Tissues

Biological tissues, which may be preserved in the claimed solutions, include any tissue that is appropriate for implantation into humans or animals. The implantable tissue can be human or non-human, such as bovine, porcine, or non-human primate, in origin. Suitable tissues include, but are not limited to, partial organs, blood cells, blood proteins, heart valve leaflets, heart valves, aortic roots, aortic walls, pulmonary valves, pulmonary conduits, non-valved conduits, mitral valves, monocusps, tendons, ligaments, fascia, large and small vascular conduits, blood vessels, arteries, veins, diaphragm, pericardium, umbilical cords, and dura mater or tympanic membranes. Especially preferred tissues suitable for cryopreservation in the claimed solutions are collagen-rich tissues, such as heart valves, vessels or conduits suitably applicable to blood vessel replacement or repair, and tendons.

Preferably, the tissue is in a "hydrated" state, defined herein as being at least 50% water by weight, but including at least 8% solids by weight. Thus, in a preferred aspect, if the tissue was fully dehydrated, it would loose at least 50% of its original weight while retaining at least 8% of its original weight.

While the tissue may be decellularized prior to preservation in the claimed solutions, the solutions may also be used to cryopreserve non-decellularized (living) tissues.

Cryopreservation Solutions

Preferably, biocompatible cryopreservation solutions in accordance with the present invention are solutions that when added to a tissue and frozen, protect the tissue from ice crystals, irradiation, and other damage resulting from freezing, sterilization, storing, and thawing of the tissue. In this manner, the cryopreservation solutions minimize the deleterious effects of cryopreservation and sterilization. Preferably, the solution is filtered through a low-porosity membrane to effect its sterilization.

Bio-Compatible Buffer

Preferable cryopreservation solutions embodying features of the present invention include a bio-compatible buffer system and more preferably an isotonic buffer system. Any buffer system that maintains a physiologically acceptable pH, from about pH 6 to about pH 8, under the varying temperature conditions the tissue is subjected to before, during, and after freezing and that is compatible with the other solution constituents and the tissue may be used.

Preferable buffers include phosphate buffers, such as phosphate-buffered saline (PBS); organic buffers, such as N-(2-hydroxyethyl)piperazine-N'-(2-ethanesulfonic acid) (HEPES) buffered saline, morpholine propanesulfonic acid (MOPS) buffered saline, and tris(hydroxymethyl) aminomethane (TRIS) buffered saline; and saline buffers such as borate, bicarbonate, carbonate, cacodylate, or citrate ions; or mixtures thereof. More preferred bio-compatible buffers include PBS, HEPES buffered saline, TRIS buffered saline, and mixtures thereof. Presently, an especially preferred buffer system uses phosphate-buffered saline to maintain pH from about 7 to about 8, more preferably at about 7.4 at about 25° C.

Preferably, cryopreservation solutions embodying aspects of the present invention include concentrations from 5 to 200 mM and more preferably from 15 to 100 mM of the bio-compatible buffer. Presently, an especially preferred solution includes a concentration from 20 to 75 mM of the bio-compatible buffer. The type and concentration of bio-compatible buffer used may be optimized to maintain the desired pH depending on the other solution constituents, including whether the radical scavenger is acidic or basic in nature.

Preferable cryopreservation solutions may also include sodium chloride as part of the bio-compatible buffer. While sodium chloride is preferred, any other salt that provides the solution with the desired ionic strength and that is compatible with the other solution constituents may be used. Preferable solutions have a concentration from 0.02 to 0.5 M and more preferably from about 0.07 to about 0.3 M sodium chloride. Presently, an especially preferred solution includes a concentration of about 0.154 M sodium chloride Cell-Impermeant Constituent Cryopreservation solutions embodying features of the present invention include a cell-impermeant constituent that is compatible with the other solution constituents. While not wishing to be bound by any particular theory, the cell-impermeant constituent is believed to reduce damage to the surface of the tissue during freezing and thawing.

Preferably, the cell-impermeant constituent has an increased hydrophobic nature in relation to the other solution constituents. While not wishing to be bound by any particular theory, it is believed that the cell-impermeant constituent forms a thin film on the surface of the tissue and may protect the surface of the tissue from abrasion and deformation that could otherwise occur when the crystalline ice matrix forms during freezing. The cell-impermeant constituent may also modify the response of the external membrane of the tissue to changes in osmotic pressure and ionic strength of the cryopreservation solution during freezing and thawing.

While any cell-impermeant constituent that is compatible with the other solution constituents and the tissue to be preserved may be used, preferable cell-impermeant constituents include, but are not limited to, proteins, serums, monosaccharides including sucrose, trehalose, polysaccharides including dextran, agrose, and alginate, long-chain polymers including polyvinylpyrrolidones (PVP), hydroxyethyl starch (HES), derivatives thereof, and mixtures thereof. More preferred cell-impermeant constituents include polyvinylpyrrolidones, hydroxyethyl starches, their derivatives, and mixtures thereof. At present, polyvinylpyrrolidone having a molecular weight of about 17,000 (weight average) is an especially preferred cell-impermeant constituent. Although FBS may be used in addition to or as a replacement for these cell-impermeant constituents, preferable cryoprotectant solutions in accord with the present invention do not include FBS.

Preferably, cryopreservation solutions embodying aspects of the present invention include from 5 to 30% and more preferably from 8 to 18% cell-impermeant constituent. In an especially preferred embodiment, the cryopreservation solution includes from 10 to 14% of a cell-impermeant constituent.

Cell-Permeant Constituent

Cryopreservation solutions embodying features of the present invention include a cell-permeant constituent that preferably serves as an intracellular or tissue-permeating cryoprotectant. While not wishing to be bound by any particular theory, the cell-permeant constituent is believed to perform at least two desirable functions regarding preservation of the tissue.

First, due to the cell-penetrating ability of the solvent, in addition to functioning to protect the exterior surfaces of the tissue during freezing, it can replace water in the interior of the tissue. By replacing at least a portion of the water in the interior of the tissue, it is believed that the formation of the crystalline ice matrix during freezing is interrupted due to interference with the hydrogen-bonding interaction between individual water molecules. Thus, damage to the water containing interstices of the tissue may be reduced because at least a portion of the water does not crystallize and expand upon freezing. Additionally, by reducing ice formation, it is believed that less water is transported out of the cells during freezing, thus reducing tissue damage from osmotic dehydration.

A second desirable feature of the cell-permeant constituent is its ability to lower the freezing point of the cryopreservation solution in relation to water. Preferable cell-permeant constituents are also miscible in water.

While any cell-permeant constituent that is compatible with the other solution constituents and the tissue to be preserved may be used, preferable cell-permeant constituents include, but are not limited to alcohols, such as propanediol, isopropanol, ethanol, t-butanol, mannitol, and glycerol; glycols, such as ethylene glycol and propylene glycol; trimethylamine; acetate; aldoses; ketones; xylose; erythrose; arabinose; ribose; glucose; fructose; galactose; and mixtures thereof. More preferred cell-permeant constituents include isopropanol, ethanol, and mixtures thereof. At present, isopropanol is an especially preferred cell-permeant constituent.

The cell-permeant constituent constitutes from 5 to 30% (v/v), more preferably from 10 to 20% (v/v) of cryopreservation solutions embodying aspects of the present invention. In an especially preferred aspect, the cell-permeant constituent constitutes about 15% (v/v) of the solution.

Radical Scavenger

A radical scavenger is included in cryopreservation solutions embodying aspects of the present invention to reduce tissue damage from energetic free-radicals that form during irradiative sterilization of the tissue. While not wishing to be bound by any particular theory, these radical species are believed to form in the fluid boundary layer surrounding the tissue, even at cryogenic temperatures.

Not only may free-radicals cause crosslinking, oxidation, and other damage during irradiation, but long-lived (persistent) radicals may be formed that cause additional damage during thawing of the tissue. As previously mentioned, when the tissue thaws, the mobility of any persistent radicals present in the frozen matrix can increase, potentially increasing the amount of tissue damage.

Radical scavengers undergo rapid reaction with free-radicals to form benign side products. Preferably, radical scavengers combine with the radiation generated radicals at a faster rate than the rate at which the radicals react with the tissue. In another aspect, the radical scavenger used in a cryopreservation solution combines with the radiation generated radicals at a faster rate than the other solution components. In general, the rate at which a radical scavenger will combine with a radical can be estimated from its single electron reduction potential. The higher the reduction potential for a specific compound, the faster it will combine with the free radical, thus deactivating its tissue-harming ability.

Preferable radical scavengers for use in the present invention are acids and salts that ionize in water. Preferable radical scavengers include, but are not limited to, sodium ascorbate, carotenoids, 1-ascorbic acid, d-isoascorbic acid, sodium sulfite, sodium metabisulfite, sulfur dioxide, nicotinic acid, nicotinic acid amine, cysteine, glutathione, sodium nitrate, sodium nitrite, flavonoids, selenium, alpha-lipoic acids, acetyl cysteine, water-soluble tocopherol derivatives including sodium Vitamin E phosphate (VEP), lauryl imino dipropionic acid tocopheryl phosphate, tocopheryl glucoside, tocopheryl succinate, Tocophersolan (tocopheryl polyethylene glycol 1000 succinate), Tocophereth-5,10,12,18, and 50 (polyethylene glycol (PEG) tocopheryl ethers), Lazaroids, ubiquinone (coenzyme $Q_{10}$) butylated hydroxytoluene (BHT), butylated hydroxyanisole (BHA), analogs thereof, isomers thereof, derivatives thereof, and mixtures thereof. More preferred radical scavengers include sodium ascorbate, water-soluble derivatives of ascorbate, carotenoids, and mixtures thereof. At present, an especially preferred radical scavenger for use in the claimed solutions is sodium ascorbate.

Preferably, cryopreservation solutions embodying aspects of the present invention include a concentration of from 0.1 to 1.5 M and more preferably from 0.3 to 1 M of the radical scavenger. Presently, especially preferred solutions include a concentration of about 0.5 M of the radical scavenger.

Benefits of the present cryopreservation solution in relation to conventional solutions may include, but are not limited to: tissue protection from ice crystal growth during freezing and thawing; regulation of pH during freezing and thawing; reduction of water activity; free-radical scavenging; and freezing point depression to −30° C. and below. In addition to radical scavenging, the solution allows for ionizing radiation to be applied to tissues at cryogenic temperatures, thus, further reducing damage to tissues and their constituents, such as collagen. It is believed that by reducing the mobility (diffusivity) of the radicals in the frozen matrix, their ability to inflict tissue damage is reduced.

Cryopreservation

Cryopreservation as applied to implantable tissues includes the general steps of (1) preparing the cryopreservation solution; 2) preparing the tissue with the cryopreservation solution; (3) freezing the tissue; (4) optionally sterilizing the frozen tissue; (5) storing the frozen tissue; and (6) thawing the tissue. After harvesting, the tissue is directly cryopreserved or processed in one of several manners, including decellularization, and then cryopreserved. Cryopreservation can immediately follow decellularization, or can occur later.

If living, non-decellularized tissue, such as a portion of an organ, is cryopreserved, viability may be reduced during sterilization. Viability refers to the ability of frozen and thawed tissue to perform its normal function in a living organism. Generally, preferable freezing and thawing profiles are based on the type of tissue being preserved and the specific cryopreservation solution. During thawing, additional constituents may be added to further reduce tissue damage.

Preferably, the cryopreservation solution may be added to the tissue in one step or in multiple steps of increasing solution constituent concentration. For example, in one aspect, a cryopreservation solution containing 15% cell-permeant constituent is added in a single step. In another aspect, a solution containing, for example, 5% of a cell-permeant constituent is added. As the tissue is cooled, a solution containing 10% of a cell-permeant constituent is added. As the tissue is cooled further, a solution containing 15% of a cell-permeant constituent is added. By increasing the cell-permeant constituent concentration as the temperature is decreased, osmotic shock to the tissue may be reduced.

By deaerating (reducing the dissolved oxygen content) the cryopreservation solution, tissue damage from the generation of oxygen radicals during later sterilization may be reduced. Thus, in one aspect, the cryopreservation solution is degassed under vacuum prior to addition to the tissue. Alternatively, the solution is not degassed. In another aspect, the tissue is also maintained under reduced pressure during the freezing process to further reduce dissolved oxygen. In yet another aspect, the cryopreservation solution itself or the solution/tissue combination may be deaerrated by passing an inert gas, including, but not limited to, nitrogen, argon, or helium, through the solution. By sparging the solution with an inert gas, dissolved oxygen can be removed. Vacuum or inert gases may be used alone or in combination to lower the oxygen content of the solution and/or the solution/tissue combination.

Lowering the temperature of the cryopreservation solution/tissue combination to below the freezing point or glass transition temperature of the cryopreservation solution (freezing) may be accomplished with any cryo-cooling system known to those of ordinary skill in the art. In one aspect, the temperature of the solution/tissue combination is lowered to at least the glass transition temperature of the cryopreservation solution. Preferably, freezing is initiated within 20 to 60 minutes after addition of the cryopreservation solution and more preferably, within 30 to 40 minutes. The water to ice phase change may be initiated from −2° C. to −6° C. by a burst of liquid nitrogen, addition of a sterile ice crystal, or vibration.

The cooling rate from 0° to −80° C. is preferably from −0.4° to −3° C. per minute. Slower cooling rates, from −0.1° to −0.3° C. per minute, for example, are also acceptable. However, slower cooling rates may lead to excessive osmotic dehydration of the tissue. More rapid cooling rates, such as from −3.5° to −30° C. per minute and faster, can result in a decrease in tissue viability.

Once the tissue has reached about −80° C., the hard-frozen tissue can be transferred to a low temperature (about −130° to about −200° C.) storage unit. In one aspect, extended storage at temperatures above about −70° C. results in tissue degradation. Extended storage at temperatures above about −130° C. may result in migratory ice recrystallization and tissue degradation.

The cryopreserved tissue is preferably packaged prior to freezing and irradiation. Packaging may occur before or after freezing. Suitable packaging materials include, but are not limited to, high-density polyethylene, foil/polyolefin, foil/polyester, and laminates, such as, polyolefin/nylon/polyester film (MYLAR®). Preferably, the package is in the form of one or more envelopes, which may be evacuated prior to closure.

In an especially preferred aspect, a package that includes three separate envelopes is used. In this aspect, the tissue and cryopreservation solution is sealed in an inner envelope that can be made of a material that is completely impermeable to bacteria. This inner envelope may then be placed in an intermediate envelope that is also impermeable to bacteria and that can be equipped with a peel-back flap. The intermediate envelope may then be placed in an outer envelope that is impermeable to bacteria and liquid nitrogen. A more detailed discussion of three-envelope packages may be found in U.S. Pat. No. 5,257,692, incorporated by reference in its entirety, except that in the event of any inconsistent disclosure or definition from the present application, the disclosure or definition herein shall prevail.

If packaging occurs prior to freezing, the package may be evacuated and the solution degassed prior to closure. In one embodiment, package evacuation and degassing occur simultaneously under vacuum.

Sterilization

Cryopreserved tissue is preferably sterilized by subjecting the tissue to ionizing radiation while at cryogenic temperature. Irradiation is performed at cryogenic temperature to reduce the damaging effects of the radiation on the tissue while affording sufficient effect on the contained microorganisms and contaminants to render the tissue sterile.

Preferably, irradiation is carried out by positioning the cryopreserved tissue in a gamma irradiation sterilizing apparatus relying on $Co^{60}$ as a source. In a preferred aspect, the cryopreserved tissue is irradiated with 5,000 to 8,000,000 rads, more preferably with 600,000 to 2,500,000 rads of gamma radiation. Preferably, the gamma radiation is applied at a rate of about 0.38 to about 0.45 Mrad/hr.

Thawing

After cryopreservation and optional sterilization, the tissue is thawed prior to implantation. While implantation is not required to immediately follow thawing, the tissue may degrade if too much time elapses. Although any suitable thawing method may be used, in one aspect, tissue that was stored at about −80° C. is thawed by placing the hard-frozen tissue in a bath of warm liquid, preferably from 4° to 42° C. and more preferably from 37° to 42° C. The liquid volume of the thawing bath can vary considerably, depending on whether the bath is temperature-controlled. In another aspect, if the tissue was stored at about −135° C. or less, the tissue may be allowed to warm more slowly in room temperature air until it reaches about −120° C., before being transferred to a liquid thawing bath.

In a preferred aspect, the package containing the tissue is completely submersed in the thawing bath until ice is no longer present. At this point, the tissue may be removed using sterile techniques and placed in mannitol and/or a cell-impermeant constituent in a bio-compatible buffer. Any non-cell membrane permeable biocompatible sugar, polyol, or other organic solute can be substituted for mannitol, such as sucrose, sorbitol, trehalose, fructose, glucose, raffinose, maltose, xylitol, amino acids, and the like.

Differential Scanning Calorimetry

The thermal denaturation temperature of a tissue is believed to depend upon the structure of its constituents. Crosslinking can affect the structure of a tissue. For connective tissues that are composed primarily of collagens, the degree of crosslinking among the collagen proteins is believed to affect the structure, and thus the denaturation temperature of the tissue. When similar denaturation temperatures are obtained for tissues, the tissues are believed to have a similar structure. By comparing the denaturation temperature of living tissues, with thawed, cryopreserved, and irradiated tissues, an estimate can be made regarding the degree of structural change that occurred during cryopreservation and sterilization.

A convenient method of determining the denaturation temperature of a tissue is through Differential Scanning Calorimetry (DSC). DSC is a common analytical method for polymer characterization. A more complete discussion of DSC and it use in the analysis of biopolymers can be found in Biomaterials, 23(6), 1503–10 (Mar. 23, 2002) and in J. Chem. Phys., 98:11, 8970–77 (1993).

Fresh, viable connective tissues have DSC denaturation temperature values ranging from about 65 to about 68° C. Connective tissues crosslinked with glutaraldehyde have elevated denaturation temperatures of about 77° C., while degraded tissues have denaturation temperatures of less than 65° C. In one aspect, tissues that have been cryopreserved in cryopreservation solutions embodying aspects of the present invention, sterilized, and thawed have denaturation temperatures that are reduced or increased by no more than about 3° C. as compared to the same type of native tissue. Native tissues are those that have been harvested, but not irradiated or cryopreserved.

The preceding description is not intended to limit the scope of the invention to the preferred embodiments described, but rather to enable a person of ordinary skill in the art of tissue cryopreservation to make and use the invention. Similarly, the examples below are not to be construed as limiting the scope of the appended claims or their equivalents, and are provided solely for illustration. It is to be understood that numerous variations can be made to the specific solutions and procedures below, which lie within the scope of the appended claims and their equivalents.

EXAMPLES

Example 1

Preparation of a Cryopreservation Solution

A solution in accordance with the present invention was made by combining the following constituents in sterile, deionized water:
sterile phosphate buffered saline (Biowhitakker, #17-516Q),
0.154 M NaCl,
12.5% (w/v) polyvinylpyrrolidone (PVP, polyvinylpyrrolidone polymer (KOLLIDONE®) 17 PF, BASF Corporation, General Office, (318) 861-8201, 8800 Line Aye, Shreveport, La. 71106),
15% (v-v) isopropanol, and
0.5 M sodium ascorbate. Molarities are for the total cryopreservation solution.

The PVP-17 was added in two steps to sterile phosphate buffered saline. After each addition the solution was mixed to completely dissolve the PVP-17. Following the complete dissolution of the PVP-17, the sodium ascorbate was added and mixed until dissolved. The solution was brought to an intermediate volume and the isopropyl alcohol was added and gently mixed. The final solution was sterilized by filtration using a 0.22 µm filter.

Example 2

Cryopreservation, Sterilization, and Thawing of Porcine Pulmonary Valve Leaflets Porcine pulmonary valve leaflets were placed in the cryopreservation solution prepared in Example 1. Decellularized porcine pulmonary heart valves were washed in 100 mL of DPBS without $Ca^{2+}$ or $Mg^{2+}$ for a minimum of one hour. The leaflets were excised from the valves. Individual leaflets from the same valve were placed into a 4×6" polyester bag with 80 mL of either a conventional DMSO/FBS cryoprotectant solution or the solution prepared in Example 1 and heat sealed. This pouch was placed into a larger foil bag and the outer pouch was heat sealed. The packages were placed in an ice-water bath for approximately 45 minutes prior to initiation of cryopreservation.

The freezing cycle was then initiated in a Controlled Rate Freezer, Model 101A (Cryomed, Mt. Clemens, Mich.). Other cryogenic freezers known to those of ordinary skill in the art may also be used. The cooling regimen began with the tissues equilibrating with the cryopreservation solution from Example 1 for approximately 45 minutes in an ice-water bath. The tissues were then slowly cooled to below 0° C. and then rapidly cooled to near liquid nitrogen temperature. Finally, the tissues were slowly cooled to the final freeze temperature before being transferred to liquid nitrogen.

The frozen packages were exposed to a gamma radiation source for a total dose between 25 and 40 kGy. Each tissue was rapidly thawed by submersion of the package in a 36–38° C. water bath for approximately 15 minutes.

Example 3

Comparative Denaturation Temperature DSC Data for fresh porcine pulmonary valve leaflets, valve leaflets thawed after conventional cryopreservation and irradiation in DMSO/FBS, and valve leaflets thawed after cryopreservation and irradiation in a cryopreservation solution embodying features of the present invention.

| Tissue Condition | Denaturation Temperature |
| --- | --- |
| Fresh | 65.87 ± 0.70° C. |
| Conventional DMSO/FBS | 63.71 ± 0.36° C. |
| Example 1 Solution | 67.53 ± 0.48° C. |

As can be seen from the comparison, there is an approximate 2° difference in the denaturation temperature between the fresh and conventional or Example 1 solutions. While the denaturation temperature of the conventional and Example 1 cryopreserved tissues changed in relation to the fresh tissue, the change was comparable, at about 2° C. This establishes that a solution in accord with the present invention performs at least as well as the conventional DMSO/FBS solution.

Example 4

Cryopreservation, Sterilization, and Thawing of bovine tendons. Bovine tendons were cryopreserved, sterilized and thawed using the same general procedure described in Example 2 for porcine pulmonary valve leaflets.

Example 5

Comparative Denaturation Temperature DSC Data for fresh bovine tendons, tendons thawed after conventional cryopreservation and irradiation in DMSO/FBS, and tendons thawed after cryopreservation and irradiation in a cryopreservation solution embodying features of the present invention.

| Tissue Condition | Denaturation Temperature |
| --- | --- |
| Fresh | 65.11 ± 0.94° C. |
| Conventional DMSO/FBS | 61.93 ± 1.29° C. |
| Example 1 Solution | 62.85 ± 1.34° C. |

These results establish that for cryopreserved and irradiated tendons, the Example 1 Solution appears to perform similarly to the conventional DMSO/FBS solution.

As any person of ordinary skill in the art of tissue cryopreservation will recognize from the provided description, figures, and examples, modifications and changes can be made to the preferred embodiments of the invention without departing from the scope of the invention defined by the appended claims.

What is claimed:

1. A method of preparing a preserved tissue, comprising
providing an uncrosslinked tissue selected from the group consisting of heart valve leaflets, aortic roots, aortic walls, pulmonary valves, pulmonary conduits, non-valved conduits, mitral valves, monocusps, tendons, ligaments, fascia, blood vessels, arteries, veins, ureters, diaphragm, pericardium, umbilical cords, dura mater, and tympanic membranes;
providing an aqueous solution comprising between 15 mM and 100 mM bio-compatible buffer; between 5% and 30% polyvinylpyrrolidone (v/v); between 5% and 30% isopropanol (v/v); and between 0.1 M and 1.5 M ascorbate;
combining the aqueous solution with the uncrosslinked tissue;
lowering the temperature of the resulting composition to at least the freezing point of the aqueous solution; and
irradiating the tissue with ionizing radiation to produce a preserved tissue,
wherein the denaturation temperature of the preserved tissue, when thawed, is reduced or increased by no more than 3° C. as compared to the uncrosslinked tissue prior to combination with the aqueous solution.

2. The method of claim 1, wherein the uncrosslinked and the aqueous solution are placed in a package before freezing.

3. The method of claim 1, wherein said aqueous solution is degassed.

4. The method of claim 1, further comprising subjecting said preserved tissue to extended storage and subsequently thawing said preserved tissue.

5. The method of claim 1, wherein said ionizing radiation is an electron beam.

6. The method of claim 1, wherein said ionizing is gamma radiation.

7. The method of claim 6, wherein said gamma radiation is administered to said uncrosslinked tissue at a rate from about 0.38 to 0.48 Mrad/hr.

8. The method of claim 6, wherein a total of from 5,000 to 8,000,000 rads is administered to said tissue.

9. The method of claim 1, further comprising packaging said uncrosslinked tissue.

10. The method of claim 9, wherein after said packaging step, said uncrosslinked tissue is sterilized.

11. The method of claim 1, further comprising lowering the temperature of said aqueous solution and said uncrosslinked tissue to at least −18° C.

12. The method of claim 1, wherein the temperature of said aqueous solution and said uncrosslinked tissue is lowered to at least −130° C.

13. The method of claim 1, wherein the temperature of said aqueous solution and said uncrosslinked tissue is lowered to at least the glass transition temperature of the aqueous solution.

14. The method of claim 1, wherein the temperature of said aqueous solution and said uncrosslinked tissue is lowered to a cryogenic temperature.

15. The method of claim 1, wherein the bio-compatible buffer maintains the pH of said aqueous solution from about 6 to about 8 before, during, and after freezing.

16. The method of claim 1, wherein the bio-compatible buffer is isotonic.

17. The method of claim 1, wherein the bio-compatible buffer comprises a buffer selected from the group consisting of phosphate-buffered saline, N-(2- hydroxyethyl)piperazine-N'-(2-ethanesulfonic acid) buffered saline, morphine propanesulfonic acid buffered saline, tris(hydroxymethyl) aminomethane buffered saline, borate buffered saline, bicarbonate buffered saline, carbonate buffered saline, cacodylate buffered saline, citrate ion buffered saline, and mixtures thereof.

18. The method of claim 1, wherein the bio-compatible buffer comprises a buffer selected from the group consisting of phosphate-buffered saline, N-(2-hydroxyethyl)piperazine-N'-(2-ethanesulfonic acid) buffered saline, tris(hydroxymethyl) aminomethane buffered saline, and mixture thereof.

19. The method of claim 1, wherein the bio-compatible buffer comprises phosphate-buffered saline.

20. The method of claim 19, wherein the bio-compatible buffer maintains the pH of said aqueous solution from about 7 to about 8.

21. The method of claim 19, wherein the bio-compatible buffer maintains the pH of said aqueous solution at about 7.4.

22. The method of claim 1, wherein the bio-compatible buffer has a concentration of from 20 to 75 mM in said aqueous solution.

23. The method of claim 1, wherein the bio-compatible buffer further comprises sodium chloride.

24. The method of claim 23, wherein the sodium chloride has a concentration of from 0.02 to 0.5 M in said aqueous solution.

25. The method of claim 23, wherein the sodium chloride has a concentration of about 0.154 M in said aqueous solution.

26. The method of claim 1, wherein the aqueous solution comprises between 10% and 14% polyvinylpyrrolidone (v/v).

27. The method of claim 1, wherein the aqueous solution comprises about 15% isopropanol (v/v).

28. The method of claim 1, wherein the aqueous solution comprises about 0.5 M ascorbate.

* * * * *